United States Patent [19]

Aberson et al.

[11] 4,103,062
[45] Jul. 25, 1978

[54] ABSORBENT PANEL HAVING DENSIFIED PORTION WITH HYDROCOLLOID MATERIAL FIXED THEREIN

[75] Inventors: Gerhard M. Aberson, Downers Grove; Emily M. Stulgate, Oak Park, both of Ill.

[73] Assignee: Johnson & Johnson, New Brunswick, N.J.

[21] Appl. No.: 695,683

[22] Filed: Jun. 14, 1976

[51] Int. Cl.² .............................................. B32B 5/16
[52] U.S. Cl. .................... 428/283; 128/284; 128/296; 156/279; 156/282; 264/131; 264/134; 264/324; 428/288; 428/409; 428/507
[58] Field of Search ............... 428/218, 283, 296, 409, 428/288, 507; 156/279, 282, 62.2; 264/324, 327, 131, 134, 136; 128/284, 285, 287, 290 R, 296, 270

[56] References Cited

U.S. PATENT DOCUMENTS

| 2,905,568 | 10/1959 | Burgeni | 427/369 |
|---|---|---|---|
| 2,955,641 | 10/1960 | Burgeni | 428/338 |
| 3,017,304 | 1/1962 | Burgeni | 428/167 |
| 3,141,809 | 7/1964 | Di Maio et al. | 428/218 |
| 3,420,235 | 1/1969 | Harmon | 128/290 R |
| 3,545,441 | 12/1970 | Gravdahl | 428/218 |
| 3,591,448 | 7/1971 | Elmendorf | 428/218 |
| 3,670,731 | 6/1972 | Harmon | 128/287 |
| 3,797,496 | 3/1974 | Loracono | 128/296 |
| 3,888,257 | 6/1975 | Cook et al. | 128/296 |
| 3,936,555 | 2/1976 | Smith | 428/218 |
| 3,965,904 | 6/1976 | Mesek et al. | 128/284 |

Primary Examiner—James J. Bell

[57] ABSTRACT

A densified bonded layer is formed in a panel of fluffed wood pulp fibers having particulate hydrocolloid material distributed therein by passing the panel between first and second compression means to apply pressure to the panel, at least one of the compression means being heated. By suitably selecting the temperature and pressure applied to the panel, an integral, densified, compacted, porous, absorbent fibrous layer or region having relatively high cohesive strength, relatively good capillarity, relatively good shape and volume stability and relatively high fluid retentivity can be formed therein. Particles of the hydrocolloid material are fixed within the panel by being bonded to the fibers substantially throughout the panel, and by mechanical entrapment between fibers in the densified bonded layer.

8 Claims, 6 Drawing Figures

ABSORBENT PANEL HAVING DENSIFIED PORTION WITH HYDROCOLLOID MATERIAL FIXED THEREIN

BACKGROUND OF THE INVENTION

This invention relates to absorbent fibrous bodies and a method of making such bodies. More particularly, this invention pertains to absorbent components suitable for use in sanitary napkins, surgical dressings, compresses, disposable diapers, hospital underpads and other products for absorption of body fluids.

Products designed to absorb body fluids generally contain as a principal component thereof an absorbent panel, batt, pad or core. These panels or batts are normally made of layers of loosely compacted, absorbent fibers, such as carded cotton webs, air-laid cellulose fibrous webs, comminuted wood pulp batts, or like materials which are highly absorbent, fluffy and porous. Unfortunately, these loosely compacted fibrous absorbent bodies possess numerous disadvantages, such as low cohesive strength, poor shape and volume stability, low capillarity, low fluid retentivity and low absorptive capacities under conditions of use.

These fluffy, porous, absorbent fibrous components have the aforementioned shortcomings because of their loosely compacted structure. When a fluid is deposited on the surface of such a component, saturation conditions are reached very quickly at the site of immediate application. At the same time, however, the adjacent portions remain relatively unsaturated and, in some instances, dry due to the low capillarity of the fibrous body. Consequently, a highly localized fluid condition results.

When water-insoluble but absorbent particulate matter, such as hydrocolloid particles, are incorporated into a loosely compacted absorbent panel, in order to enhance the moisture retention thereof, these particles tend to "dust out" of the panel.

Commonly assigned U.S. Pat. Nos. 2,905,568, 2,955,641, and 3,017,304 to Burgeni describe a method by which the tensile strength of loose cellulosic fibrous fluff can be improved. According to the teachings of these patents, a controlled amount of water or an aqueous binder solution (between 0.0005 gms./cm.$^2$ and 0.03 gms./cm.$^2$) can be applied to one surface of the loose fiber mass, followed by a compacting pressure of between 5 psi and 100 psi to produce a densified bonded surface fiber structure or skin of water-induced, paper-like bonds, hereinafter sometimes referred to as a "Burgeni layer." Panels having a Burgeni layer have relatively good strength, good shape and volume stability and high fluid retentivity.

It has now been found, however, that a densified, absorbent fibrous layer can be produced in a pulp panel or batt without an external application of a water spray or the like as taught in the aforementioned Burgeni patents, and that during the formation of the densified layer hydrocolloid particles can be fixed within the panel to further enhance the fluid retentivity thereof.

SUMMARY OF THE INVENTION

According to the present invention, a densified bonded layer or region can be formed in an air-laid panel or batt of fluffed wood pulp fibers and containing particulate hydrocolloid material and inherent moisture by simultaneously subjecting both sides of the panel or batt to a predetermined pressure and at a predetermined temperature differential. Hydrocolloid particles are thereby fixed in the panel by mechanical entrapment in the densified layer and/or by individual bonding to cellulosic fibers substantially throughout the batt.

Suitable compression means for this purpose may comprise a pair of platens, calender rolls, or other means. By suitably selecting the temperature and the applied pressure, an integral, densified, compacted, porous, absorbent fibrous layer or region is formed in the panel having relatively high cohesive strength, relatively good capillarity, relatively good shape and volume stability, and relatively high fluid retentivity.

When one or both panel surfaces are subjected to pressure at an elevated temperature, the densified layer or region is produced within the panel. When one of the panel surfaces is subjected under pressure to a relatively higher temperature and the other panel surface is subjected to a relatively lower temperature, the densified layer or region is formed near to the panel surface subjected to the relatively lower temperature. Additionally, it has been found that at a temperature differential of at least about 40° F. or higher, the densified layer or region will be produced at the relatively colder panel surface. To produce the densified region or layer at approximately the mid-plane of the panel, both panel surfaces are subjected under pressure to about the same elevated temperature. To obtain the greatest degree of bonding and mechanical entrapment of hydrocolloid particles, it is desirable to produce the densified layer in the portion of the panel having the greatest concentration of hydrocolloid particles.

For the purposes of the present invention the temperature of at least one panel surface should be elevated to an extent sufficient to induce migration of inherent moisture away from that particular surface. The elevated temperature should be less than the boiling temperature of water at the ambient pressure, however. For producing a densified panel surface layer or skin at ambient atmospheric pressure, preferably one surface of the panel is subjected to a temperature of about 210° F. and the other panel surface is subjected to a temperature of about 80° F., i.e., a temperature differential of about 130° F. is maintained.

The compaction pressure to which the panel is subjected during the aforementioned heat-induced densification can vary over a relatively wide range; however, the panel should be subjected to a pressure of about 4 kg./cm.$^2$ to about 15 kg./cm.$^2$.

Hereinafter, the densified bonded layer or region formed by subjecting air-laid cellulose fiber panels to compaction pressure at an elevated temperature will be sometimes referred to as a "heat-induced densified bonded layer."

Prior art panels having a water-induced Burgeni layer typicaly have a thin, well-defined dense and strongly bonded fiber layer adjacent to the fiber fluff and have only a relatively minor transition between the two extremes. The thin dense layer does not permit a suitable distribution or fixation of hydrocolloid particles in the panel. Also, inasmuch as the strength of the panel is largely determined by its densified layer, such panels may become too rigid if a relatively thick densified layer is produced in order to meet strength requirements. On the other hand, a heat-induced densified bonded layer produced according to this invention is not as strongly bonded in a single plane as the Burgeni layer, but has a transitional region; thus, great strength can be imparted to panels having a heat-induced densified bonded layer without causing the same degree of panel rigidity as in the case of panels with water-induced Burgeni layers.

It is a further feature of the present invention that relatively precise control of the degree of bonding can be obtained by using the heat-induced bonding method. Also, since the bonded layer remains relatively dry, hot melt penetration into the bonded layer for bonding the panel to a polyolefin sheet, such as a polyethylene backing sheet for a diaper, can be achieved. Moreover, other methods of adhering polyethylene backing sheets to the panel become available as a result, which feature is of particular advantage in the production of disposable diapers, or the like absorbent pads.

DESCRIPTION OF THE PREFERRED EMBODIMENTS

According to this invention, a densified bonded layer or region is formed in an air-laid, fluffed wood pulp or batt panel containing particulate hydrocolloid material and inherent moisture by simultaneously compacting the panel with a predetermined pressure and subjecting each surface of the panel to a predetermined temperature. As a result, a substantial portion of the hydrocolloid material is fixed in the panel by mechanical entrapment in the densified layer and/or by bonding to cellulosic fibers substantially throughout the batt, as will be discussed in greater detail hereinbelow. Air-laid panels suitable for the present purposes are disclosed in commonly owned U.S. Pat. No. 3,938,522 to Repke.

Figure 4:
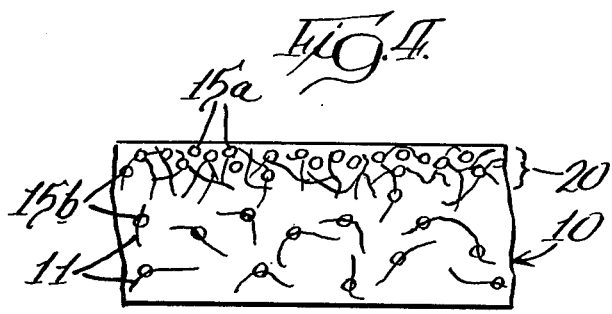
FIG. 4 is a schematic cross-sectional view of a panel having a heat-induced densified bonded layer in accordance with the present invention.
Figure 5:
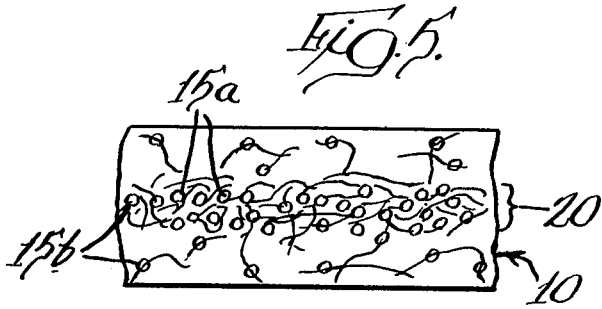
FIG. 5 is a schematic cross-sectional view of another panel having a heat-induced densified bonded layer in accordance with the present invention.

The heat-induced densified bonded layer is formed by raising the temperature of at least one surface of the panel to an extent sufficient to induce migration of inherent moisture away from that surface and into the panel. It is believed that the moisture collects at a relatively cooler region within the panel and creates a densified layer in which bonds are formed between the fibers. The moisture contributes to the bond formation, so that the most extensive bonding takes place in the relatively cooler region in the panel where a relatively greater amount of moisture collects. When one of the panel surfaces is subjected under pressure to a relatively lower temperature than the opposite panel surface, the heat-induced densified bonded layer or region is formed nearer to the panel surface subjected to the relatively lower temperature (FIG. 4). To produce the heat-induced densified bonded layer or region at the panel surface having the relatively lower temperature, the temperature differential between the panel surfaces preferably is at least about 40° F. The densified layer or region is produced at approximately the mid-plane of the panel when both panel surfaces are subjected, under pressure, to about the same elevated temperature (FIG. 5). When the panel is compressed at atmospheric pressure, it is preferable to have at least one panel surface above about 80° F. and both panel surfaces below about 210° F.

Figure 1:
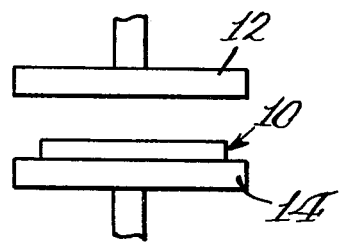
FIG. 1 is a schematic view of a typically between two compression platens in the open position.
Figure 2:
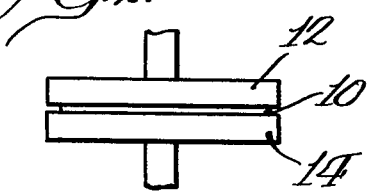
FIG. 2 is a schematic view of a panel between two compression platens in the closed position.
Figure 3:
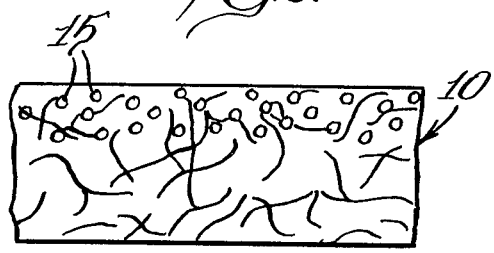
FIG. 3 is a cross-sectional view of an unbonded panel having hydrocolloid particles distributed therein.

Referring to FIGS. 1 and 2, loosely compacted wood pulp panels 10 were prepared by air-laying individualized cellulose fibers from a grinding mill (not shown) and were placed between first and second pressure means such as platens 12 and 14 of a compression press. Platens 12 and 14 have electrical resistance heaters capable of maintaining a predetermined temperature level and also have hydraulic means for exerting a predetermined pressure. As shown in FIG. 3, each panel 10 initially comprises a highly porous, loosely compacted, cellulosic fibrous batt and has low cohesive strength, relatively low capillarity, relatively poor shape and volume stability and relatively low fluid retentivity.

A predetermined quantity of hydrocolloid material, such as starch polyacrylonitrile (SPAN, manufactured by General Mills and commercially available under the designation SGR502S), can be distributed in the batt by dusting the hydrocolloid particles 15 with a "salt-shaker type" dispensing device on one surface of the panel. The batt is then pressed between platens 12 and 14. Preferably, a temperature differential is maintained between the platens, with the colder platen being juxtaposed to the panel surface that was dusted with the hydrocolloid particles and having a temperature from about 80° F. to about 170° F., and about 40° colder than the other platen. As shown in FIG. 4, a densified bonded layer is thereby formed along the panel surface which was dusted with the hydrocolloid particles.

The particulate absorbent materials contemplated herein contain water-insoluble but water-swellable polymeric substances having at least about 25 percent of their molecular structure composed of hydrophilic groups and capable of retaining water in an amount which is at least 10 times the weight of the absorbent material in dry form, and preferably about 15 to about 70 times the weight, or more.

Illustrative particulate absorbent materials that are suitable for the present purposes are powdered graft copolymers of a water-insoluble polysaccharide such as starch or cellulose having hydrophilic chains of carboxyl-, carboxylate-, and/or carbamide-bearing moieties.

Water-insoluble starch or a wide variety of cellulosic fibers can be utilized as starting materials for producing graft copolymers of this general type. Typical such cellulosic fibers are: cotton, cotton linters, wood pulp, bagasse pulp, jute, rayon, and the like. The polysaccharide chains are then modified by grafting thereon a hydrophilic chain of the general formula

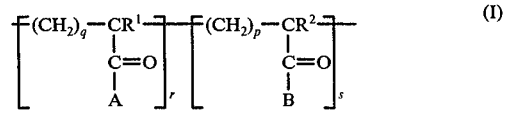

(I)

wherein A and B are selected from the group consisting of $-OR^3$, $-O(\text{alkali metal})$, $-OHNH_3$, $-NH_2$, wherein $R^1$, $R^2$ and $R^3$ are selected from the group consisting of hydrogen and alkyl having 1 to 4 carbon atoms, wherein $r$ is an integer having a value of 0 to about 5000, $s$ is an integer having a value of 0 to about 5000, r plus s is at least 500, p is an integer having a value of zero or 1, and q is an integer having a value of 1 to 4.

Preferred hydrophilic chains are hydrolyzed polyacrylonitrile chains and copolymers of polyacrylamide and sodium polyacrylate. In another preferred embodiment both ionizable polymeric moieties and non-ionizable polymeric moieties can be grafted on the same polysaccharide backbone.

While the detailed mechanism by which the grafting of the hydrophilic chain or chains onto a starch or a cellulosic backbone is not fully known, it is believed that grafting takes place through a free radical mechanism whereby the free radical is situated on the backbone which serves as a reducing agent, and the hydrophilic chain is attached to the starch or cellulosic reducing agent through a carbon linkage. The produced graft copolymer using a cellulosic backbone is of the type

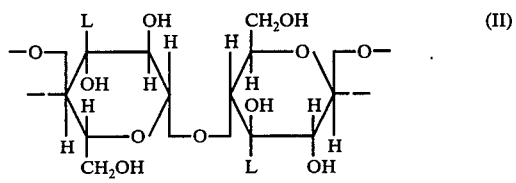

(II)

wherein L represents the hydrophilic chain of Formula I, above. The graft copolymer using a starch backbone is substantially similar to that represented by Formula I except that a starch backbone is present in lieu of a cellulosic backbone.

It is a feature of this invention that a substantial portion of the hydrocolloid particles are fixed in the batt after the densified bonded layer is formed, thereby obviating the prior art problem of hydrocolloid particles "dusting out" of the panels. As shown in FIGS. 4 and 5, some hydrocolloid particles 15a are fixed in panel 10 by mechanical entrapment through the action of fibers 11 in the densified bonded layer 20, and other hydrocolloid particles 15b are fixed in panel 10 by bonding to cellulosic fibers 11 substantially throughout the thickness of panel 10.

Presumably, the bonds between hydrocolloid particles 15b and fibers 11 are formed in the same manner and at the same time as the heat-induced fiber-to-fiber bonds in the panel. Bonds between fibers 11 are formed substantially throughout the batt, and most extensively in the relatively cooler region of the panel where the densified bonded layer is formed. Due to the similarity of the molecular structure of the cellulosic fibers and the hydrocolloid particles, bonding takes place therebetween upon the application of heat and pressure, thereby fixing the hydrocolloid particles in the panel. Thus, it is desirable to form the densified bonded layer in the portion of the panel containing the greatest amount of hydrocolloid particles. Where the hydrocolloid particles are dusted on one surface of the panel, it is therefore preferred to apply the relatively colder platen to that surface.

Other hydrocolloid particles are fixed in panel 10 by mechanical entrapment through the action of fibers 11 when forming densified layer 20. Substantially all of the mechanical entrapment is in the densified layer 20 where the density of fibers 11 is such that hydrocolloid particles 15a are held in place through the action of a plurality of fibers 11.

The heat-induced densified layer is more advantageous than the water-induced densified layer as taught by Burgeni in the aforementioned patents because a more diffuse layer is formed, as opposed to the skin layer formed by Burgeni. This enables a greater amount of hydrocolloid particles to be fixed in place through bonding and/or mechanical entrapment.

The minimum distributed moisture content needed to form a densified, bonded layer depends on the temperature differences between the surfaces of the panel, on the panel basis weight, as well as on the desired thickness and density of the densified layer. Preferably the panel or batt has a moisture content of at least about 2.5 wt. percent. In any event, however, the moisture content of the air-laid panel or batt should be sufficient to cause the formation of a densified layer when the moisture is concentrated in a predetermined region within the panel or batt in a manner described herein. When necessary, the moisture content of the panel or batt can be enhanced by exposing the panel or batt to a humid atmosphere, to a fine aqueous mist or spray which penetrates the panel, or to steam prior to compaction at elevated surface temperatures.

The compaction pressure to which the panel is subjected can vary over a wide range, but should be at least about 2 kg./cm.$^2$ and preferably in a range of about 6 kg./cm.$^2$ to about 10 kg./cm.$^2$. The time period during which the panel is maintained under pressure is a less important variable, since an increase in time under pressure from 3 seconds to 30 seconds has been found not to substantially alter the properties imparted to the panel.

The heat-induced densified bonded layer can be formed in a wood pulp panel whether or not hemicelluloses are present in the panel. In addition, the wood pulp panels can also contain natural or synthetic fibers such as silk, wool, linen, nylon and/or cellulose acetate fibers in combination with the cellulosic fibers as long as the cellulosic fibers constitute at least about 50 percent of panel weight.

As disclosed in commonly assigned copending U.S. patent application Ser. No. 695,682 now abandoned to Aberson et al. and filed concurrently herewith, a densified bonded layer can be formed in air-laid panels by subjecting the panels to a predetermined pressure at predetermined temperatures at both surfaces for a predetermined time period. As shown in FIG. 4, when at least one of the platens was heated above room temperature, and a temperature differential of at least about 40° F. was maintained between the panel surfaces, an air-laid panel specimen having an inherent moisture content of about 5 percent to about 6 percent by weight showed, after three seconds of pressing, a bonded layer at the panel surface that contacted the platen having the relatively lower temperature. When both platens were heated to the same elevated temperature between slightly above room temperature and about 210° F., a bonded layer was created approximately in the midplane of the panels 10, as shown in FIG. 5.

However, when a panel was dried at about 300° F. to a moisture content of approximately zero percent and was subsequently pressed between platens 12, 14 with platen 12 at about 210° F. and platen 14 at approximately 170° F., no bonded layer could be observed at the panel surfaces. It is therefore thought that the original inherent moisture content, for example between about 5 percent by weight and about 6 percent by weight of the air-laid panel, contributes to the fiber bond formation, and that the temperature difference between the platens causes the moisture to migrate to and concentrate at the surface of the colder platen.

When the platens are at the same elevated temperature, the moisture is believed to concentrate at a mid-plane of the panel where a heat-induced densified bonded layer is formed.

The heat-induced bonded layer increases the strength of the panel as will be discussed in greater detail hereinbelow. Also, any undisintegrated wood pulp clumps present in the panel comprise localized areas of high basis weight which are placed under considerable stress during the pressing procedure. After release of the pressure, these localized areas tend to remain compacted and are visible as relatively flat dense, compressed fiber regions in the panel while the fiber fluff in the surrounding area is relaxed and expands again. The compacted areas or regions associated with the compressed undisintegrated pulp can be within or outside of the densified bonded layer and act like rivets enhancing panel stability, thus in some instances it is desirable to have a certain amount of clumps present in the panel.

Changes in pressure significantly affected the formation of densified bonded layer 20, when compaction was carried out at an elevated temperature, although during compaction at room temperature little effect was observed from increases in pressure. Varying the time period under pressure was the least significant variable affecting formation of the densified bonded layer 20, since a ten-fold increase in time (from three seconds to thirty seconds) resulted in a relatively small increase in the strength of panels 10.

As is also disclosed in the above-mentioned copending application, temperature is an important variable regarding the formation of the densified bonded layer 20 in panel 10. When both platens had the same temperature, the panels attained an optimum strength when the platens, and thus the panel surfaces, were held at a temperature of about 210° F. It is thought that at platen temperatures in excess of 210° F. (i.e., at or about the boiling point of water at ambient atmospheric pressure), moisture concentration does not take place under the test conditions, thereby resulting in a decrease of tensile strength.

When the platens had different temperatures, the densified bonded layer 20 formed against the colder platen. It has been found that the strongest densified bonded surface layer is formed when one platen is maintained at a temperature of about 210° F. and the opposite platen is maintained at a temperature of about 170° F. When the temperature of one of the platens exceeds 210° F., the panel strength drops rapidly.

The densified bonded surface layer 20 formed with the platens at diffent temperatures was smooth and in some respects resembled the Burgeni type of water-induced bonded surface layers which are formed, for example, by spraying one gram of water on eleven inch by fourteen inch panels; however, the panel produced according to the present invention was not as rigid and exhibited a substantial transition region adjacent to the densified layer.

When one platen was at about 210° F. and the other platen was at about 170° F., the eight ounce per square yard panels having a heat-induced densified bonded surface layer were at least as strong as the eight ounce per square yard panels having Burgeni layers. For panels having a Burgeni layer, panels having a basis weight of four ounces per square yard were consistently stronger than panels having a basis of weight of eight ounces per square yard. However, panels having a heat-induced densified bonded layer had a greater strength at basis weights of eight ounces per square yard than at four ounces per square yard. This indicates the importance of the presence of moisture in the air-laid fiber fluff, because there is a greater absolute amount of moisture available in the eight ounce per square yard panel for concentration in the plane where the densified bonded layer is formed.

When the wet strengths of some of the panels were determined, it was found that panels with a Burgeni layer and panels with the strongest heat-induced densified bonded layers all exhibited a wet strength similar to an unbonded panel. These results indicate that both the Burgeni method and the heat-induced method of creating densified bonded layers may involve the formation of hydrogen bonds which are known to break down when the moisture content becomes too high.

Additional tests indicated that a heat-induced densified bonded layer could be formed in a fiber fluff consisting of nearly pure cellulose and without the presence of thermoplastic hemicellulose. The densified bonded layer 20 was formed in a wood pulp panel (made from sulfite pulp derived from Southern United States pine and commercially available under the designation "Placetate-F" from ITT Rayonier, Inc.) having a basis weight of 13.0 ounces per square yard and an alpha-cellulose content of greater than 98 percent so that it was essentially free of hemicelluloses. The formation of the densified bonded layer indicated that the presence of hemicelluloses is not essential for the bond formation. The Placetate-F panel was compared with another wood pulp panel (made from sulfate pulp derived from Southern United States pine and commercially available under the designation "Rayfloc-J" from ITT Rayonier, Inc.) having a basis weight of 8.1 ounces per square yard and an alpha-cellulose content of about 88 percent and a relatively high hemicellulose content. The Placetate-F wood pulp fluff had a tensile strength approximately equal to the tensile strength of the Rayfloc-J panel; however, the Placetate-F panels had a higher basis weight.

Since the heat-induced bonding method produces a densified bonded layer in a panel in the dry state, it is possible to heat-bond the thermoplastic polyethylene backing sheet to the densified layer of the panel. After a heat-induced densified bonded layer was formed in the panel against the colder platen, an embossing plate was placed against one of the platens and the platen was heated to 230° – 240° F., the softening temperature of polyethylene being about 235° F. The opposite platen was heated to about 210° F. to prevent the formation of a heat-induced bonded layer at the back side of the panel. The panel was pressed between the platens with the polyethylene sheet against the embossing plate and the densified bonded layer of the panel against the polyethylene sheet. The applied pressure was about 1 kg./cm.$^2$. The bonding of the polyethylene sheet against the densified bonded layer of the panel preferably should take place rapidly to prevent shrinkage of the polyethylene sheet.

The absorption capacity of panels produced according to the present method was determined by measuring the maximum amount of 1.7 percent aqueous NaCl solution that could be held by a wood pulp panel under a given load. An increase in the temperature and stress involved in the formation of a heat-induced densified bonded layer in a panel both resulted in a reduction of the liquid holding capacity of the panel. From the liquid holding capacity standpoint, the most desirable properties were achieved when one platen was at a temperature of about 170° F. to about 200° F. and the other platen was at about room temperature.

The relationship between the liquid absorption capacity of the panels and the dry tensile strength of the panels is such that a gain in the dry tensile strength is obtained at the expense of a decrease of the absorption capacity of a panel. The absorption capacity is lowest for a given dry tensile strength when both platens are at the same elevated temperatures.

It should be noted that the ability of the panel to spread and distribute the liquid is another important consideration in rating panel absorption performance, and panels having heat-induced densified bonded layers exhibit an ability to distribute liquid through the panel which is at least comparable to that of a panel having a Burgeni layer. Panels incorporating hydrocolloid particles and having heat-induced densified bonded layers displayed a similar distribution of liquid in the panel and held the liquid with greater tenacity.

To determine the ability of a panel to spread and distribute liquid, diaper panels which were eleven inches by fourteen inches were placed on a polyethylene film with the densified bonded layer nearer to the film. A line was drawn parallel to the panel width and through the center of the panel to divide the panels into two equal halves. On each half, two lines were drawn, one line on each half being two inches from and parallel to the center line, and the second line being drawn on each half four inches from the center line. Thus, the 14 inch long panel was divided into six sections, the end sections furthest removed from the center line being three inches by eleven inches, and the four sections between the end sections each being two inches by eleven inches.

The panel and polyethylene film were positioned with one-half of the panel horizontal and the other half on a 60° inclined plane so that the panel was folded at 60° along the center line parallel to the width. A piece of diaper facing was folded in place on the partially inclined panel.

A burette was used to dispense a dyed aqueous saline solution on the center of the sixty degree fold. Three portions of 50 ml. of liquid were dispensed at 3 minute intervals. Three minutes after the last portion of liquid was released, the facing sheet was removed and the wet panel was cut along the five lines drawn on the panel surface. The resulting six panel sections were individually weighed, oven dried, and weighed again to determine the quantity of liquid which was absorbed in each section. Thus, the actual weight of the migrated liquid was determined for each section.

The data in Table I (below) represents the weight of liquid found in each panel section expressed as a percent of the total weight of liquid added during the test. The columns headed #1 in Table I contain the results of the two inch by eleven inch panel sections closest to the center fold; columns #2 show the results of the next two inch by eleven inch sections, and columns #3 show the results of the three inch by eleven inch sections. The heat-induced densified bonded layers in panels without hydrocolloid particles and in panels including hydrocolloid particles were formed with the top platen at 85° F., the other platen at 205° F., and 8.5 kg./cm.$^2$ of pressure. The water-induced Burgeni layer was formed with both platens at 80° F., one gram of water sprayed on the 11 inch by 14 inch panel, and 8.5 kg./cm.$^2$ of pressure.

From a liquid spreading or wicking standpoint, the best panel is one that can absorb the most liquid away from the center section of the panel, particularly up the inclined plane against opposing gravity forces. Wood pulp panels of Rayfloc-J having a basis weight of 275 gm./m.$^2$ were tested for liquid wicking and the data is presented in Table I. The data in the top three rows of Table I, below, shows that the extent of liquid spreading or liquid wicking in panels with a heat-induced densified bonded layer with hydrocolloid particles and without hydrocolloid particles were approximately equal to that in panels with water-induced Burgeni layers. The panels were prepared in the platen press under 8.5 kg./cm.$^2$ of pressure for three seconds. Similar results were obtained with panels produced under different pressure conditions.

Table I

| Panel Description | Comparison of Amount of Liquid Absorbed in Various Panels | | | | | | Tensile Strength gm./cm. Width |
|---|---|---|---|---|---|---|---|
| | Percent Absorbed, by Weight of Panel | | | | | | |
| | Inclined Plane | | | Horizontal Plane | | | |
| | #3 | #2 | #1 | #1 | #2 | #3 | |
| Heat-induced layer with SPAN hydrocolloid | 8 | 10 | 17 | 20 | 19 | 26 | — |
| Heat-induced layer | 7 | 10 | 18 | 21 | 17 | 27 | 207 |
| Water-induced layer | 6 | 9 | 18 | 21 | 19 | 27 | 142 |
| Polyethylene embossed to panel | 2 | 8 | 20 | 25 | 23 | 22 | — |

Figure 6:
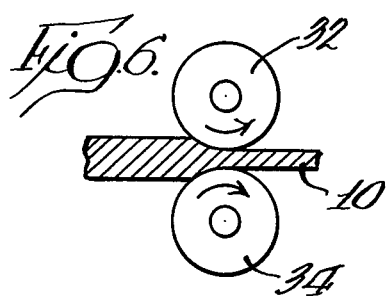
FIG. 6 is a schematic illustration of an alternate embodiment for the production of panels embodying the present invention.

Panels having a heat-induced densified bonded layer 20 can also be produced at high speed by employing first and second compression means which comprise upper and lower calender rolls 32, 34 (FIG. 6) as opposed to upper and lower platens 12, 14 (FIGS. 1 and 2). The calender rolls may be heated (or cooled) as desired to provide the necessary temperature conditions at the panel surfaces. Where both calender rolls are at the same temperature, the panels 10 which are produced will have a densified bonded layer along a mid-plane of the panel, and when one of the calender rolls has a relatively higher temperature than the other calender roll, the panels 10 will have a densified bonded layer along the surface thereof which is contacted by the colder calender roll.

Under the static conditions of the platen press (FIGS. 1 and 2), the surface temperature of the platens closely approximates the surface temperature of the panel surfaces, thus when a platen press is utilized for the production of heat-induced densified layers the platen surface temperature can be taken as the surface temperature of the panel contiguous therewith. However, under the dynamic conditions of a continuously rotating calendering operation a higher roll surface temperature may be required, depending on the contact time with the panel surfaces, to transfer sufficient heat into the panel to concentrate the moisture contained in the air-laid panel into the bonding plane at which the densified bonded layer is formed. Since the rate of heat transfer is proportional to the temperature difference between each calender roll and the panel, the optimum surface temperature of each calender roll is a function of the speed at which the panel travels between the calender rolls and can be readily ascertained for a given set of operating parameters.

The present invention can also be practiced in combination with a water-induced densified layer as taught by Burgeni in the aforementioned patents. For example, by spraying water onto the pulp panel surface that will contact the relatively colder platen or calender roll, a dense, water-induced skin layer will be produced on that particular surface and a relatively more diffuse heat-induced dense layer will be produced in the pulp panel between the surfaces contacted by the platens or calender rolls.

While this invention is susceptible of embodiment in many different forms, there has been shown in the drawings and has herein been described in detail preferred embodiments, with the understanding that the present disclosure is to be considered as an exemplification of the principles of the invention and is not intended to limit the invention to the embodiments illustrated.

We claim:

1. An absorbent fibrous structure suitable for use as an absorbent component in absorbent products comprising: a cellulosic fibrous batt having a first portion which is a highly porous, loosely compacted, region of relatively low cohesive strength, relatively low capillarity, relatively poor shape and volume stability and relatively low fluid retentivity, and a second portion which is a densified, compacted, porous, absorbent fibrous region having relatively high cohesive strength, relatively good capillarity, relatively good shape and volume stability and relatively high fluid retentivity, said second portion being integrally connected to said first portion of said batt, and a particulate hydrocolloid material distributed in at least one of said portions of said fibrous batt and fixed therein by bonding to cellulosic fibers in said batt.

2. The absorbent fibrous structure as defined in claim 1 wherein said first portion has a plurality of localized, relatively denser fiber concentrations distributed therein.

3. The absorbent fibrous structure as defined in claim 1 wherein hydrocolloid material is distributed in said second portion and is mechanically entrapped within said second portion.

4. The absorbent fibrous structure as defined in claim 1 wherein said hydrocolloid material is distributed throughout said batt and is bonded to cellulosic fibers in said batt substantially throughout said batt and is mechanically entrapped within said second portion.

5. The absorbent fibrous structure as defined in claim 1 wherein said hydrocolloid material is a water-insoluble polysaccharide containing hydrophilic chains.

6. The method as defined in claim 5 wherein said polysaccharide is starch polyacrylonitrile.

7. The absorbent fibrous structure as defined in claim 1 wherein said first portion of said batt is disposed on one side only of said second portion of said batt.

8. The absorbent fibrous structure as defined in claim 1 wherein said second portion is disposed at an intermediate location within said batt.

* * * * *